United States Patent [19]

Bloch et al.

[11] Patent Number: 5,352,797

[45] Date of Patent: Oct. 4, 1994

[54] SILANE-TYPE COUPLING AGENT, PROCESS FOR ITS PREPARATION, AND ITS USE FOR THE PRODUCTION OF A CONDUCTING COATING ON GLASS

[75] Inventors: Bertrand Bloch; André Attias, both of Paris; Jacques Ancelle, Chatenay Malabry; Claude Andrieux; Pierre Audebert, both of Paris, all of France

[73] Assignee: Office National d'Etudes et de Recherches Aerospatiales, Chatillon Sous Bagneux, France

[21] Appl. No.: 30,239

[22] PCT Filed: Oct. 1, 1991

[86] PCT No.: PCT/FR91/00770

§ 371 Date: Mar. 30, 1993

§ 102(e) Date: Mar. 30, 1993

[87] PCT Pub. No.: WO92/06100

PCT Pub. Date: Apr. 16, 1992

[30] Foreign Application Priority Data

Oct. 3, 1990 [FR] France ................................ 90 12201

[51] Int. Cl.$^5$ .......................................... C07D 207/325
[52] U.S. Cl. .................................................. 548/406
[58] Field of Search ............................ 549/4; 548/406

[56] References Cited

U.S. PATENT DOCUMENTS

3,346,588  10/1967  Ashby ................................. 548/406
5,066,748  11/1991  Nagasubramanian et al. ...... 526/258

FOREIGN PATENT DOCUMENTS

1184098  2/1959  France .

OTHER PUBLICATIONS

Journal of the American Chemical Society, vol. 104, No. 7, Apr. 7, 1982, Gaston, Pa. US, pp. 2031–2034.
Chemistry Letters, No. 4, Apr. 1984, Tokyo, JP, pp. 509–512.

Primary Examiner—Johann Richter
Assistant Examiner—Fiona T. Powers
Attorney, Agent, or Firm—Armstrong, Westerman, Hattori, McLeland & Naughton

[57] ABSTRACT

The coupling agent is comprised of a pyrrolidyl group capable of being incorporated in the chain of an electroconducting polymer, and a silane group —Si(OR$^1$)$_3$ which may be chemically bound to a glass substrate in order to form an adherent coating of said polymer. It is obtained by an addition reaction implementing an epoxide function and a primary or secondary amine function.

9 Claims, No Drawings

SILANE-TYPE COUPLING AGENT, PROCESS FOR ITS PREPARATION, AND ITS USE FOR THE PRODUCTION OF A CONDUCTING COATING ON GLASS

The invention relates to a silane-type compound which can be used as a coupling agent, comprising a functional group capable of reacting in order to be incorporated in the chain of an electrically-conducting polymer, it being possible for the silane group, for its part, to be chemically bonded to an inorganic substrate, especially glass, in order to form an adherent coating of this polymer.

In accordance with a usage established in industry, "silane" here refers to a compound containing a group $-Si(-OR^1)_3$, $R^1$ being a monovalent radical and more particularly an alkyl radical.

The compound according to the invention has the formula:

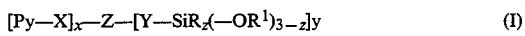  (I)

in which Py represents the pyrrolidyl radical

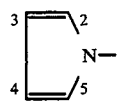

which may be substituted in position 3 and/or 4, X and Y represent bivalent radicals, Z represents an at least bivalent radical, R and $R^1$ represent monovalent radicals, $(x+y)$ being equal to the valency of Z and z being between 0 and 2.

The invention is targeted in particular at a compound having the following formula:

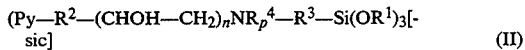  (II)

in which $R^2$ and $R^3$ each represent a bivalent radical, $R^4$ represents a monovalent radical or a hydrogen atom, n is equal to 1 or 2 and p is equal to 2-n.

In a specific example of the compound according to the invention, $R^1$, $R^2$ and $R^3$ respectively represent the $C_2H_5$, $CH_2$ and $(CH_2)_3$ radicals, and n is equal to 2.

The invention is also targeted at a coupling agent having the following formula:

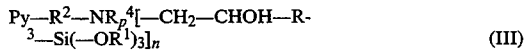  (III)

in which $R^1$ and $R^3$ each represent a bivalent radical, $R^4$ represents a monovalent radical or a hydrogen atom, n is equal to 1 or 2 and p is equal to 2-n.

Another subject of the invention is a process for the preparation of the compound defined above, in which two molecules containing mutually reactive groups are reacted together, one of these molecules additionally containing a pyrrolidyl group and the other containing a group $-SiR_z(OR^1)_{3-z}$.

Advantageously, the mutually reactive groups are an amine group and an epoxide group.

By way of example, the molecules used in the process according to the invention may be

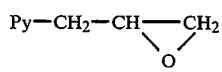  (IV)

and $NH_2-(CH_2)_3-Si-(OCH_2CH_3)_3$ (V).

The molecule of the formula (IV) above may be obtained in particular by introducing pyrrole dropwise into an aqueous reaction mixture containing sodium hydroxide, tetrabutylammonium hydrogensulfate and epichlorohydrin, which is stirred vigorously and cooled so as not to exceed room temperature.

Alternatively, the molecules used may be, on the one hand, commercial silane containing an epoxide functional group:

  (VI)

and, on the other hand, one of the following compounds:

  (VII)

  (VIII).

The molecule of the formula (VII) is easily prepared according to the process described by Foulds in Anal. Chem., 60, 2473 (1988). The molecule of the formula (VIII) can likewise be obtained according to the process described in European Patent Application 338,989.

The invention is also targeted at the use of the compounds of formula (I) defined above for the production of an electrically-conducting coating which adheres to an inorganic substrate, for example made of glass or silica, by formation of covalent bonds between the silicon atoms of the compound and the surface of the substrate, and oxidation of the pyrrolydyl [sic] groups of the compound and of an additional pyrrole in order to form a polymer which includes the compound and to make this polymer conducting. This additional pyrrole may be pyrrole properly so called or a pyrrole which is substituted at one or both of the positions β to the nitrogen atom.

In a more detailed way, the use according to the invention provides that the alkoxysilane groups of the compound (I) are hydrolyzed in a water/alcohol solution, that the substrate is immersed in the solution, that the treated substrate is then immersed in an aqueous ferric chloride solution and that the additional pyrrole is introduced therein while stirring vigorously.

In a variation of the use according to the invention, instead of reacting the preconstituted compound according to the invention with the substrate, a molecule containing the pyrrolidyl radical is reacted with the substrate which has been treated beforehand with a commercial silane, this molecule and this silane containing mutually reactive groups.

The substrate may be especially a fibrous reinforcer, for example in the woven form, for a composite material. The invention then makes it possible to adjust the electrical properties of this composite material.

EXAMPLE 1

Synthesis of a molecule containing a reactive epoxide group and a pyrrolidyl group.

A reaction mixture formed from 200 g of sodium hydroxide NaOH, 8.4 g of tetrabutylammonium hydrogensulfate, 200 ml of water and 125 ml of epichlorohydrin is stirred very vigorously at room temperature in a one liter reactor. 40 g of freshly distilled pyrrole are added dropwise while cooling the solution with a bath of ice-cold water in order to keep the temperature of the mixture between 15° and 20° C. The mixture is left stirring with a stream of nitrogen for 3 hours, 100 ml of ether are added in order to cause an aqueous phase and an organic phase to settle which are separated from each other. The aqueous phase is extracted twice with 100 ml of ether. The whole of the organic phase is washed with aqueous salt solution until neutrality, dried over a molecular sieve, filtered and distilled under vacuum. 58 g of N-glycidylpyrrole

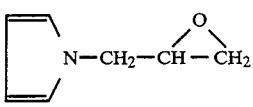

or a yield of 80%, are obtained. The product is characterized by $^1$H NMR and $^{13}$C NMR. Its purity is 93%; it is determined by liquid phase chromatography.

EXAMPLES 2 AND 3

Synthesis of the compound of formula (II).

This synthesis is carried out by reacting the molecule obtained in Example 1 with (3-aminopropyl)triethoxysilane NH$_2$—(CH$_2$)$_3$Si—(OCH$_2$CH$_3$)$_3$, a commercial product commonly designated by the reference A1100.

EXAMPLE 2

2.21 g (0.01 mol) of A1100 and 2.46 g (0.02 mol) of the N-glycidylpyrrole obtained in Example 1 are mixed in a suitably dried 50 ml round-bottomed flask. The mixture is brought to 60° C. under a stream of nitrogen. The progress of the reaction is monitored by size exclusion chromatography. At the end of 6 hours, the compound [Py—CH$_2$—CHOH—CH$_2$N—(CH$_2$)$_3$—Si(OCH$_2$CH$_3$)$_3$ is obtained, all the N-glycidylpyrrole having been consumed. The compound is characterized by $^1$H NMR. Its purity is 83%, determined by chromatography.

EXAMPLE 3

The preparation is carried out as in Example 2, the reaction being carried out for 5 days at room temperature. A virtually identical result is obtained.

EXAMPLES 4 and 5

Synthesis of the compounds containing a reactive amine group and a pyrrolidyl group.

EXAMPLE 4

Synthesis of the compound of formula (VII).

A suspension of 0.6 g of lithium aluminum hydride LiAlH$_4$ in 50 cm$^3$ of tetrahydrofuran THF is cooled to 0° C. by an ice bath, under argon. A solution of N-(2-cyanoethyl)pyrrole (1 g) in approximately 20 ml of tetrahydrofuran is added dropwise over approximately 15 minutes. The ice bath is removed and the mixture is brought to reflux for 3 hours. After hydrolysis of the excess hydride, the aqueous phases are extracted with ether mixed with 50% pentane and then purified by filtration chromatography on silica. By evaporation, an oil (0.615 g) is obtained which is characterized by $^1$H NMR and $^{13}$C NMR.

EXAMPLE 5 Synthesis of the compound of formula (VIII).

22 g (0.25 mol) of N-methyl-1,3-propanediamine are run in dropwise into a 250 ml round-bottomed flask equipped with a reflux condenser, a dropping funnel and a nitrogen inlet and containing 125 ml of acetic acid, while stirring vigorously and while maintaining the temperature at around 15° to 20° C. 33 g (0.27 mol) of 2,5-dimethoxytetrahydrofuran are then run in. The mixture is brought to reflux for 30 minutes, the progress of the reaction being monitored by NMR. The mixture is distilled under water pump vacuum and 90 ml of acetic acid and methanol are recovered. The mixture is brought to a pH of 10 by addition of a concentrated sodium hydroxide solution. The mixture is extracted with 125 ml of chloroform. The aqueous phase is washed several times with chloroform. The organic phases are combined, the majority of the chloroform is removed on a rotary evaporator and then distillation is carried out under pump vacuum. The compound of formula (VIII), identified by $^1$H NMR and infrared (n$_{20}$$^D$=1.498), is obtained with a yield of 46%.

EXAMPLES 6 TO 8

Synthesis of the coupling agents of formula (III).

EXAMPLE 6

2.76 g (0.02 mol) of the compound obtained in Example 5 and 4.72 f [sic] (0.02 mol) of (3-glycidyloxypropyl)trimethoxysilane (GLYMO) are mixed in a suitably dried 50 ml round-bottomed flask. The mixture is brought to 60° C. under a stream of nitrogen. The progress of the reaction is monitored by size exclusion chromatography. At the end of 5 hours, the compound Py—(CH$_2$)$_3$—N(CH$_3$)—CH$_2$-CHOH—CH$_2$—O—(CH$_2$)$_3$—Si—(OCH$_3$)$_3$ is obtained, all the silane having been consumed. The compound obtained and [sic] characterized by $^1$H NMR, its purity being 85% by chromatography.

EXAMPLE 7

The preparation is carried out as in Example 6, the reaction being carried out for 5 days at room temperature. Virtually the same result is obtained.

EXAMPLE 8

The preparation is carried out as in Example 6 from a mixture of 1.24 g (0.01 mol) of the compound obtained in Example 4 and of 4.72 g (0.02 mol) of (3-glycidyloxypropyltrimethoxysilane (GLYMO). The compound obtained, characterized by $^1$H NMR, has a purity of 90% by chromatography.

EXAMPLES 9 TO 14

Production of a conductive coating on a glass substrate.

The production of a conductive coating from the compound prepared in one of Examples 2, 3, 6, 7 or 8 is carried out in two stages.

In a first stage, the silane group is hydrolyzed in water/alcohol medium, according to processes which correspond substantially to those described in the literature and relating to commercially-available silanes. The parameters which have a significant influence on the result are the concentration of the silane in the solution, the pH and the age of the solution. The inorganic substrate is then placed in the solution for a suitable period of time, rinsed and dried.

In a second stage, the material treated above is immersed in an aqueous solution containing an oxidizing agent which causes polymerization of the pyrroles and a doping agent which makes the polypyrroles obtained conductive, the oxidizing agent generally constituting, at the same time, the doping agent. An aqueous solution of pyrrole is added in a single step with stirring. The parameters to take into account are the concentration of oxidizing and/or doping agents, and of pyrrole, in the solutions, as well as the treatment time. The treated material is rinsed copiously with water. Without knowing the exact thickness of the coating, the surface resistivity in "ohms per square" of the product is determined. The resistance between two parallel electrodes is measured using an ohmmeter, this resistance is multiplied by the length of the electrodes and divided by the distance between them.

EXAMPLE 9

0.1 g of the silane obtained in Example 2 is introduced into 10 ml of a mixture containing equal volumes of water and isopropanol. After 2 to 5 minutes, a glass pane measuring 7.5 cm×2.5 cm×0.1 cm, degreased beforehand with methylene chloride, is immersed in the mixture, where it is left for 30 minutes. The pH of the solution is of the order of 9 to 10. The pane is rinsed with water and brought in an oven to 110° C. for 1 hour. The pane thus treated is immersed in 50 ml of a 0.05M aqueous ferric chloride solution, slightly acidified with acetic acid, and then 50 ml of a 0.02M aqueous solution of freshly distilled pyrrole is run in in a single step while stirring. At the end of 4 hours, the pane is coated with a homogeneous uniform layer of a conductive coating which is black in color. After rinsing with water, the resistivity has a value 4.5 megohms per square.

EXAMPLE 10

The coating is carried out as in Example 9, bringing the concentrations of the ferric chloride and pyrrole solutions to 0.3M and 0.1M respectively. At the end of 15 minutes, 45 minutes and 2 hours, resistivities of 71 kiloohms per square, 8 kiloohms per square and 1.8 kiloohms per square are obtained respectively.

EXAMPLE 11

The coating is carried out as in Example 9, bringing the concentrations of the ferric chloride and pyrrole solutions to 1M and 0.4M respectively. At the end of 5 minutes and 15 minutes, resistivities of 20 kiloohms per square and 1.7 kiloohms per square are obtained respectively.

EXAMPLE 12

The starting point is a 5 cm×5 cm piece of glass fabric coated with a so-called textile oil, which is removed by a heat treatment of 30 minutes at 500° C. The coating is then carried out as in Example 9, the concentrations of the ferric chloride and pyrrole solutions being 0.08M and 0.04M respectively. At the end of one hour, a resistivity of 39 kiloohms per square is obtained.

EXAMPLE 13

The coating is carried out as in Example 12, the concentrations of the ferric chloride and pyrrole solutions being brought to 1M and 0.4M respectively. At the end of 15 minutes, a resistivity of 100 ohms per square is obtained.

EXAMPLE 14

A 20 cm×20 cm piece of commercially available glass fabric, already treated with the silane A1100, is used as the substrate. 2 g of N-glycidylpyrrole are dissolved in 100 ml of methylene chloride in a 21 cm crystallizer. The fabric is immersed several times in the solution, until the latter has been exhausted. The treated sample is then placed in an oven at 70° C. for 6 hours. At the end of this treatment, the fabric is rinsed with acetone and then with water and placed in a 2 liter beaker containing one liter of a 0.3M ferric choride [sic] solution, acidified with 5 cm$^3$ of acetic acid. One liter of a 0.1M aqueous solution of freshly distilled pyrrole is run in in a single step while stirring vigorously. At the end of 20 minutes, the fabric is rinsed copiously with water and then with acetone and placed in a dessicator under pump vacuum in the presence of phosphorus pentoxide for 1 hour. The resistivity has a value 20 kiloohms per square.

COMPARATIVE EXAMPLES

By way of comparison, Examples 9 to 11 were reproduced but without the silane according to the invention. No adhesive homogeneous deposit formed on the glass pane. By replacing, in these same examples, the silane according to the invention with the commercial silane A1100, a heterogeneous layer forms which is partly removed during the rinsing operations.

EXAMPLES 12 AND 13 were also reproduced in the absence of the silane according to the invention. A black deposit was obtained with a surface resistivity greater than 20 megohms per square.

What is claimed is:

1. A compound of formula

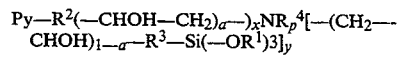

wherein

Py is the pyrrolidyl radical

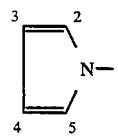

which is optionally substituted in at least one of the positions 3 and 4, $R^1$ is selected from the group consisting of $CH_3$ and $C_2H_5$, $R^2$ is selected from the group consisting of $CH_2$ and $(CH_2)_3$, $R^3$ is selected from the group consisting of $(CH_2)_3$ and $CH_2-O-(CH_2)_3$, $R^4$ is selected from the group consisting of $CH_3$ and H, a is 0 or 1, x is 1 or 2, with the proviso x is 1 is a is 0, y is 1 or 2, with the proviso that y is 1 is a is 1, and p is equal to 2-x-y.

2. A compound according to claim 1, wherein a is 1.

3. A compound according to claim 2, wherein x is 2.

4. A compound according to claim 1, wherein a is 0.

5. A compound according to claim 4, wherein y is 1.
6. A compound according to claim 2, wherein y is 2.
7. A compound according to claim 3, wherein $R^1$ is $C_2H_5$, $R^2$ is $CH_2$ and $R^3$ is $(CH_2)_3$.

8. A compound according to claim 5, wherein $R^1$ is $CH_3$, $R^2$ is $(CH_2)_3$, and $R^3$ is $CH_2-O-(CH_2)_3$.
9. A compound according to claim 6, wherein $R^1$ is $CH_3$, $R^2$ is $(CH_2)_3$, and $R^3$ is $CH_2-O-(CH_2)_3$.

* * * * *

UNITED STATES PATENT AND TRADEMARK OFFICE
CERTIFICATE OF CORRECTION

PATENT NO.  : 5,352,797
DATED       : October 4, 1994
INVENTOR(S) : BLOCH et al.

It is certified that error appears in the above-identified patent and that said Letters Patent is hereby corrected as shown below:

Column 6, line 40,
"$Py-R^2(-CHOH-CH_2)_a-)_xNR_p^4[-(CH_2-CHOH)_{1-a}-R^3-Si(-OR^1)3]_y$" should be -- $[Py-R^2(-CHOH-CH_2)_a-]_xNR_p^4[-(CH_2-CHOH)_{1-a}-R^3-Si(-OR^1)3]_y$ --.

Signed and Sealed this

Thirtieth Day of May, 1995

Attest:

BRUCE LEHMAN

Attesting Officer    Commissioner of Patents and Trademarks